United States Patent [19]

Moldt et al.

[11] Patent Number: 5,296,493

[45] Date of Patent: Mar. 22, 1994

[54] 1-SUBSTITUTED-2-(N-PHENYL-N-(PHENYL-METHYL)METHANAMINE)-4,5-DIHYDRO-IMIDAZOLES AND RELATED COMPOUNDS AND THEIR USE IN TREATING CALCIUM OVERLOAD IN BRAIN CELLS

[75] Inventors: Peter Moldt, Humlebaek; Elsebet Ø. Nielsen, Copenhagen, both of Denmark

[73] Assignee: NeuroSearch A/S, Glostrup, Denmark

[21] Appl. No.: 704,469

[22] Filed: May 23, 1991

[51] Int. Cl.$^5$ ............... C07D 233/24; C07D 233/60; C07D 233/61; C07D 401/06; A61K 31/415; A61K 31/44

[52] U.S. Cl. ................... 514/341; 514/401; 514/400; 548/335.5; 548/340.1; 548/348.1; 548/349.1; 546/278

[58] Field of Search ............ 548/353, 354, 342, 348.1, 548/349.1, 335.5, 340.1; 514/401, 400, 341; 546/278

[56] References Cited

FOREIGN PATENT DOCUMENTS 0001647 5/1979 European Pat. Off. .
0069078 1/1973 Japan .

OTHER PUBLICATIONS

B. K. Siesjö et al., Journal of Cerebral Blood Flow and Metabolism, 9, 127–140 (1989).
B. K. Siesjö, NIPS, 5, 120–125 (1990).
Winifred G. Nayler, Calcium Antagonists, Academic Press, pp. 259, and 293–297 (1988).
Merck Index (11th Edition), entry 709 on p. 107 (1989).

*Primary Examiner*—Floyd D. Higel
*Attorney, Agent, or Firm*—Gordon W. Hueschen

[57] ABSTRACT

The present patent application discloses compounds of the formula

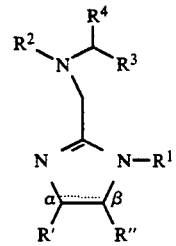

wherein
$R^1$ is $C_{1-10}$ saturated or unsaturated alkyl; or

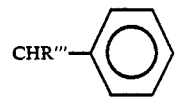

wherein $R'''$ is H or

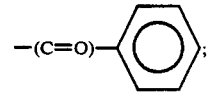

$R^2$ is phenyl which is unsubstituted or substituted one or more times with halogen, $CF_3$, $C_{1-6}$-alkoxy, $NO_2$, $CO_2$—$C_{1-6}$-alkyl, methyl; benzyl which may be substituted one or more times with halogen, $CF_3$, $C_{1-6}$-alkoxy, $NO_2$, $CO_2$—$C_{1-6}$-alkyl, methyl; pyridyl; or cyclohexyl;

$R^3$ phenyl which is unsubstituted or substituted one or more times with halogen, $CF_3$, $C_{1-6}$-alkoxy, $NO_2$, $CO_2$—$C_{1-6}$-alkyl, methyl; naphthyl which may be substituted one or more times with halogen, $CF_3$, $C_{1-6}$-alkoxy, $NO_2$, $CO_2$—$C_{1-6}$-alkyl, methyl; pyridyl; $C_{1-6}$ unsaturated alkyl; furanyl;

$R^4$ is H, $C_{1-6}$-alkyl, or benzyl; or (Abstract continued on next page.)

ABSTRACT
-continued

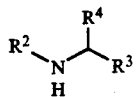

together form

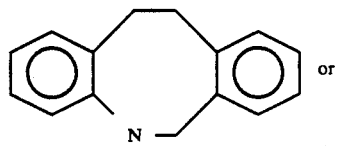 or

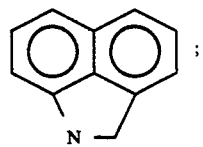 ;

R' and R" are each hydrogen or together form an extra benzo ring;

and wherein the dotted line represents an optional extra bond between the two carbon atoms designated α and β, or a pharmaceutically-acceptable addition salt thereof.

The compounds are useful as pharmaceuticals, for example in the treatment of Ca overload in brain cells.

17 Claims, No Drawings

1-SUBSTITUTED-2-(N-PHENYL-N-(PHENYLMETHYL)METHANAMINE)-4,5-DIHYDROIMIDAZOLES AND RELATED COMPOUNDS AND THEIR USE IN TREATING CALCIUM OVERLOAD IN BRAIN CELLS

The present invention relates to novel therapeutical active compounds and their use as well as to pharmaceutical preparations comprising the compounds. The novel compounds of the invention possess valuable activity as calcium overload blockers which make them useful in the treatment of anoxia, ischemia and migraine for example.

It is well known that an accumulation of calcium in the brain is seen after anoxia, ischemia, migraine and other hyperactivity periods of the brain.

An uncontrolled high concentration of calcium in the brain cells is known to cause most of the degenerative changes connected with above diseases.

Therefore compounds which can block the calcium overload of brain cells will be useful in the treatment of anoxia, ischemia, migraine and in the prevention of the degenerative changes connected with the same.

It is an object of the present invention to provide novel compounds having useful calcium overload blocking activity.

The novel compounds of the invention have the formula:

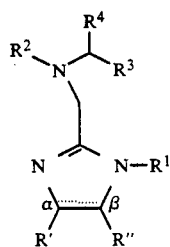

wherein
$R^1$ is $C_{2-10}$ saturated or unsaturated alkyl or

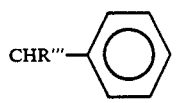

wherein $R'''$ is H or

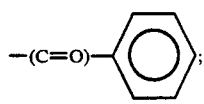

$R^2$ is phenyl which may be substituted one or more times with halogen, $CF_3$, $C_{1-6}$-alkoxy, $NO_2$, $CO_2$—$C_{1-6}$-alkyl, methyl; benzyl which may be substituted one or more times with halogen, $CF_3$, $C_{1-6}$-alkoxy, $NO_2$, $CO_2$—$C_{1-6}$-alkyl, methyl; pyridyl; or cyclohexyl;

$R^3$ phenyl which may be substituted one or more times with halogen, $CF_3$, $C_{1-6}$-alkoxy, $NO_2$, $CO_2$—$C_{1-6}$-alkyl, methyl; naphthyl which may be substituted one or more times with halogen, $CF_3$, $C_{1-6}$-alkoxy, $NO_2$, $CO_2$—$C_{1-6}$-alkyl, methyl; pyridyl; $C_{1-6}$ unsaturated alkyl; furanyl;

$R^4$ is H, $C_{1-6}$-alkyl, or benzyl; or

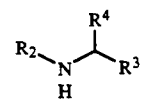

together form

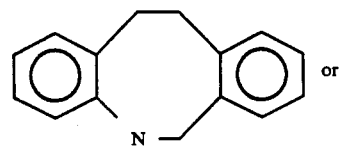

or

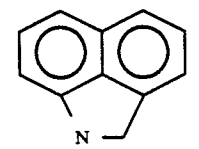

$R'$ and $R''$ are each hydrogen or together form an extra benzo ring;

and wherein the dotted line represents an optional extra bond between the two carbon atoms designated $\alpha$ and $\beta$, or a pharmaceutically-acceptable addition salt thereof.

Examples of such salts include inorganic and organic acid addition salts such as the hydrochloride, hydrobromide, phosphate, sulphate, citrate, lactate, tartrate, maleate, fumarate, mandelate, oxalate and the acetate.

The compounds can be prepared by conventional methods well known in the art. Such methods include the step of reacting a compound having the formula

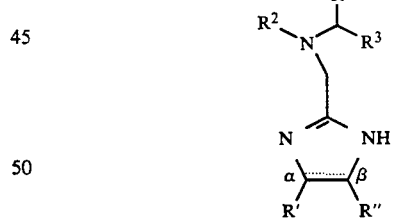

wherein $R^2$, $R^3$, $R^4$, $\alpha$, $\beta$, $R'$, $R''$ and the dotted line have the meanings set forth above, with a compound having the formula $R^1$—X wherein $R^1$ has the meaning set forth above and wherein X is a leaving group such as for example halogen, or reacting a compound having the formula

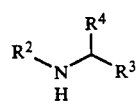

wherein $R^2$, $R^3$, $R^4$ have the meanings set forth above with a compound having the formula

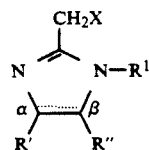

wherein $R^1$, X, $\alpha$, $\beta$, R', R" and the dotted line have the meanings set forth above, to form a compound of the invention.

The starting compounds are well known compounds.

BIOLOGY

A high influx of calcium from extracelluar compartments into neurons is seen after opening of voltage operated calcium channels. Such opening of calcium channels may be induced by depolarization of neuronal membranes.

A crude synaptosome preparation contains small vesicles surrounded by neuronal membranes, and it is possible to study an opening of the voltage operated calcium channels in such a preparation.

In the below described test influx of $^{45}Ca$ into synaptosomes is studied under depolarized conditions. The effect of test substances on the depolarization induced calcium uptake can thus be studied.

TEST PROCEDURE

The cerebral cortex from a male Wistar rat is homogenized in 20 ml ice cold 0.32M saccharose. In the following steps the temperature is kept at 0° C. to 4° C. The homogenate is centrifuged at $1,000 \times g$ for 10 minutes and the supernatant recentrifuged for 20 minutes at $18,000 \times g$. The obtained pellet is resuspended in 0.32M saccharose (10 ml per g of original tissue).

Aliquots of 0.05 ml of the hereby obtained synaptosome suspension are added to glass tubes containing 0.625 ml of a NaCl buffer (136 mM NaCl, 4 mM KCl, 0.35 mM $CaCl_2$, 1.2 mM $MgCl_2$, 20 mM Tris HCl, 12 mM glucose, pH 7.4) as well as 0.025 ml of different test substances in 48% ethanol. These tubes are pre-incubated for 30 minutes on ice and thereafter for 6 minutes at 37° C.

$^{45}Ca$ uptake is initiated by addition to above glasstubes of 0.4 ml $^{45}CaCl_2$ (specific activity: 29–39 Ci/g; (calcium chloride) 0.5 Ci per tube). For depolarized samples the 0.4 ml $^{45}CaCl_2$ contain KCl (145 mM) and for non-depolarized NaCl (145 mM). The samples are incubated for 15 seconds.

The $^{45}Ca$ uptake is stopped by filtering through glass fibre filters, which are subsequently washed 3 times with an ice cold solution of 145 mM KCl, 7 mM EGTA and 20 mM Tris HCl, pH 7.4 (5. ml). The radioactivity on the filters are measured by liquid scintillation spectrometry. Experiments are performed in duplicate.

SAMPLE PREPARATION

Above test substances are dissolved in for example 10 ml 48% ethanol at a concentration of 0.44 mg/ml. Dilutions are made in ethanol. Test substances are tested at concentrations of 0.1, 0.3, 1, 3, 10 . . . μg/ml.

RESULTS

The test value is given as $IC_{20}$, that is the concentration in μM of the test substances, which inhibit 20% of the potassium stimulated uptake of $^{45}Ca$. The uptake in potassium depolarized samples are corrected for basal uptake in non-depolarized samples. The $IC_{20}$ value is determined from a dose response curve.

The results obtained by testing selected compounds according to the invention are presented in the table below.

TABLE

| Compound | $IC_{20}$ (μM) |
| --- | --- |
| 1-benzyl-2-(2-phenyl-N-benzyl-methaneamine)-4,5-dihydro-imidazole | 0.4 |
| 1-(α-(benzoylbenzyl)-2-(N-phenyl-N-benzyl-methaneamine)-4,5-dihydro-imidazole | 0.4 |

PHARMACEUTICAL COMPOSITIONS

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredient or, more broadly, one (1) to one hundred (100) milligrams, per tablet, are accordingly suitable representative unit dosage forms.

METHOD OF TREATING

Due to the high degree of activity the compounds of the invention may be administered to a subject, e.g., a living animal body, in need of alleviation, treatment, or amelioration of an indication which is sensitive to the activity or influence of the compounds of the present invention including sensitive to the Ca overload blocking properties of the compounds of the invention. The compounds of the invention are preferably administered in the form of an acid addition salt thereof, concurrently, simultaneously, or together with a pharmaceutically-acceptable carrier or diluent, especially and preferably in the form of a pharmaceutical composition thereof, whether oral, rectal, or parenteral (including subcutaneous) route, in an effective amount. Suitable dosage ranges are 1–500 milligrams daily, preferably 1–100 milligrams daily, and especially 1–30 milligrams daily, depending as usual upon the exact mode of administration, form in which administered, the indication toward which the administration is directed, the subject involved and the body weight of the subject involved, and the preferences and experience of the physician or veterinarian in charge.

The following examples will illustrate the invention further, however they are not to be construed as limiting.

EXAMPLE 1

1-(α-Benzoylbenzyl)-2-(N-phenyl-N-(benzyl)-methanamine)-4,5-dihydro-imidazole

A mixture of 2-(N-phenyl-N-(benzyl)-methanamine)-4,5-dihydro-imidazole, hydrochloride (Antazoline)(0.6 g, 2.2 mmol), desylbromide (0.62 g, 2.2 mmol) and potassium carbonate (0.5 g) is refluxed for 1 hours in dry acetonitrile. After cooling to room temperature the reaction mixture is added 5 ml acetone and 5 ml diethylether and is filtered. The filtrate is concentrated in vacuo and the crude product is subjected to column chromatography using chloroform/methanol 7/1 as eluent. The fractions containing the product are concentrated in vacuo and on trituration with diethylether the title compound precipitates and the product is obtained as yellow crystals. Mp 91° C.

Compound 2–3 are prepared in a similar way as described above using allylbromide and propargylbromide.

1-allyl-2-(N-phenyl-N-(benzyl)-methanamine)-4,5-dihydro-imidazole, hydrochloride: Mp 177°–178° C. (The reaction mixture is stirred for 6 hours at room temperature. The product is obtained as a base and the hydrochloride is made by trituration with ethereal solution of hydrogenchloride).

1-Propargyl-2-(N-phenyl-N-(benzyl)-methanamine)-4,5-dihydro-imidazole: Mp 57°–61° C. (The reaction mixture is stirred for 6 hours at room temperature. The product is obtained as a base and the hydrochloride is made by trituration with ethereal solution of hydrogenchloride).

EXAMPLE 2 a: 1-Methyl-2-chloromethyl-imidazoline, hydrochloride

A solution of chlor-acetonitrile (6.3 ml, 0.1 mol) and absolute ethanol (5.8 ml 0.1 mol) in 120 ml absolute diethylether is added 0.17 moles dry hydrogen-chloride at 0° C. during 3 hours. The reaction mixture is kept at 20° C. over night and the precipitate is filtered off, washed with absolute diethylether and dried on an oil pump leaving chloracetimidoethylether, hydrogen chloride as a white crystalline solid.

A solution of chloracetimidoethylether, hydrochloride (1.58 g, 10 mmol) and N-methyl-ethylenediamine (0.74 g, 10 mmol) in 10 ml absolute ethanol is stirred at 0° C. and under a nitrogen atmosphere for one hour. A solution of hydrogen chloride in absolute ethanol (6.3 ml, 10 mmol) is added and the mixture is heated to 40° C. and stirred for additional two hour. After cooling to room temperature a precipitate of ammonium chloride is filtered of and the filtrate is concentrated in vacuo yielding the title compound as a yellow oil.

The following intermediates are prepared in a similar way as described above using respectively N-ethyl-ethylenediamine, N-propyl-ethylenediamine, N-butyl-ethylenediamine, N-pentyl-ethylenediamine, N-hexyle-thylenediamine, N-heptyl-ethylenediamine, N-nonyle-thylenediamine, phenylenediamine and (2-chloropropionitrile and N-butyl-ethylenediamine).

1-Ethyl-2-chloromethyl-imidazoline, hydrochloride. Yellow oil.

1-Propyl-2-chloromethyl-imidazoline, hydrochloride. Yellow oil.

1-Butyl-2-chloromethyl-imidazoline, hydrochloride. Brownish crystals. Mp 99°–102° C.

1-Pentyl-2-chloromethyl-imidazoline, hydrochloride. Slightly yellow crystals (hygroscopic).

1-Hexyl-2-chloromethyl-imidazoline, hydrochloride. Slightly yellow crystals (hygroscopic).

1-Heptyl-2-chloromethyl-imidazoline, hydrochloride. Beige crystals. Mp 105°–108° C.

1-Nonyl-2-chloromethyl-imidazoline, hydrochloride. White crystals. Mp 119°–121° C.

2-Chloromethyl-benzimidazole, hydrochloride. Mp (dec.) 210° C.

1-Butyl-2-(2-chloroethyl)-imidazoline, hydrochloride. Oil.

1-benzyl-2-chloromethyl-imidazoline, hydrochloride.

To an ice cooled solution of potassium cyanide (65 g, 1 mol) in 125 ml water, is added a mixture of formaldehyde 37% (85 ml, 1 mol) and 65 ml water, at a rate to insure that the temperature is kept below 10° C. (takes approximately 30 min). To the cooled solution is added benzoylchloride (116 ml, 1 mol) under vigourous stirring, which is continued for an additional hour. Water is added to dissolve the formed salts and the to phases are separated. The water phase is extracted repeatedly with diethylether and the combined organic phases is washed with water and brine, dried over sodiumsulphate and concentrated in vacuo. Vacuum distillation 86°–90° C./1 mbar yields benzoylglycolonitrile.

To an ice cooled solution of benzoylglycolonitrile (32.2 g, 200 mmol) and absolute ethanol (9.2 g, 200 mmol) in 50 ml absolute chloroform is added 6.1 g dry hydrogenchloride gas, and the mixture is kept at −20° C. for three days. The formed crystals are filtered of and washed with dry diethylether, and are finally dried in vacuo yielding benzoylglycolo-imidoethylether as white crystals. Mp 100°–105° C.

To an ice cooled solution of N-benzyl-ethylenediamine (7.5 g, 50 mmol) in 25 ml absolute ethanol is added in one portion benzoylglycolo-imidoethylether (12.2 g, 50 mmol) and the mixture is stirred for three hours at 0° C. and at room temperature overnight. Finally is the mixture stirred at 60° C. for three hours and is concentrated in vacuo. The remanecens is extracted four times with 30 ml boiling ethylacetate (to remove benzamide) and the product is recrystallized from ethanol yielding 1-benzyl-2-hydroxymethyl-imidazoline, hydrochloride as a crystalline compound. Mp 144°–145° C.

1-Benzyl-2-hydroxymethyl-imidazoline hydrochloride (5.66 g, 25 mmol) is on an icebath slowly added thionylchloride (3.6 ml, 50 mmol), the mixture is stirred overnight at room temperature and concentrated in vacuo. The crude product is taken up in absolute ethanol and the title compound precipitate upon addition of dry diethylether as a very hygroscopic white crystalline compound.

b: N-benzyl-4-fluoroaniline

A solution of 4-fluoroaniline (4.7 ml, 50 mmol), benzaldehyde (5.3 g, 50 mmol) and one crystal p-toluene-sulfonic acid is refluxed using a Dean-Stark ® apparatus until no more water is collected and the mixture is concentrated in vacuo. The crude product is dissolved in 100 ml 96% ethanol and added sodium borohydride (4.0 g, 100 mmol) and stirred for 1 hour. Most of the ethanol is removed in vacuo and the residue is taken up in water and 15 g of potassium hydroxide in 50 ml water is added, causing the amine to crystallize. The product is recrystallized from methanol/water (in a ratio of 4 to 1) yielding the title compound as white crystals. Mp 38°–39° C.

The following intermediates are prepared in a similar way as described above using respectively 4-fluoroaniline, acetophenone, cyclohexylcarboxaldehyde, cyclohexylamine, 2-aminopyridine, 4-trifluoromethylaniline, 4-trifluoromethyl-benzaldehyde, 5,6,7,8-tetrahydro-1-napthylamine, 2,4-dichloroaniline, 2,4-dibromoaniline, 4-methoxyaniline, 2,4-difluoroaniline, 3-methoxybenzaldehyde, 4-methoxybenzaldehyde, 3-nitrobenzaldehyde, 4-nitrobenzaldehyde, 3-nitroaniline, 2,4,6-trimethylaniline, 4-nitroaniline, cyclopropylcarboxaldehyde, 3-amino-methylbenzoate, furfural and 3-pyridine-carboxaldehyde.

N-(4'-Fluorobenzyl)-4-fluoroaniline. Mp 54°–55° C.
N-(α-Methyl-benzyl)-4-fluoroaniline. Colourless oil.
N-cyclohexylmethyl-aniline. Bp 100°–110° C./2 mbar.
N-benzyl-cyclohexylamine. Bp 100°–105° C./2 mbar.
N-benzyl-2-aminopyridine. Mp 94°–95° C.
N-Benzyl-4-trifluoromethylaniline. Mp 53°–54° C.
N-(4'-trifluoromethylbenzyl)-4-trifluoromethylaniline. Mp 58°–59° C.
N-benzyl-5,6,7,8-tetrahydro-1-napthylamine. Mp 56°–57° C.
N-benzyl-2,4-dichloroaniline. Mp 37°–38° C.
N-benzyl-2,4-dibromoaniline. Mp 35°–36° C.
N-cyclohexylmethyl-2,4-dichloroaniline. Oil.

N-benzyl-4-methoxyaniline. Mp 48°–49° C.
N-benzyl-2,4-difluoroaniline. Yellow oil.
N-(3'-methoxybenzyl)-aniline. Yellow oil.
N-(4'-methoxybenzyl)-aniline. Mp 61°–63° C.
N-(3'-nitrobenzyl)-aniline. Mp 84°–85° C.
N-(4'-nitrobenzyl)-aniline. Mp 69°–70° C.
N-Benzyl-3-nitroaniline. Mp 106°–107° C.
N-benzyl-2,4,6-trimethylaniline. Oil.
N-benzyl-4-nitroaniline. Mp 140°–141° C.
N-cyclopropylmethyl-aniline. Oil.
N-benzyl-3-carboxymethylaniline. Mp 96°–98° C.
N-(2-furanylmethyl)-aniline. Oil.
N-(3-pyridylmethyl)-aniline. Mp 66°–67° C.
N-(2-phenylethyl)-aniline.

A mixture of aniline (9.1 ml, 100 mmol), phenethylbromide 18.5 g, 100 mmol), potassiumcarbonate (13.8 g, 100 mmol) and 50 ml dimethylsulfoxide is stirred at ambient temperature for 72 hours, and is diluted with 200 ml water. The mixture is extracted three times with diethylether and the combined organic phases is washed with water and brine and dried over magnesium sulphate. The solution is concentrated in vacuo and the crude product is subjected to a vacuum distillation yielding the title compound as a colourless oil dest. 120°–128° C./0.7 mbar.

The following compound is prepared in a similar way using propargylbromide.
N-propargyl-aniline. Oil.

c: 1-Benzyl-2-chloromethyl-imidazole, oxalate

A solution of imidazole (13.6 g, 200 mmol) in 33% aqueous sodium hydroxide is heated to 100° C. for 10 min, the water is removed in vacuo and the crystalline sodium salt is dried at 0.1 mBar and 160° C. for 40 min. The salt is dissolved in 100 ml acetonitrile and is added benzylbromide 23.8 ml, 200 mmol). After stirring at 50° C. for 30 min, the mixture is concentrated in vacuo and the formed NaBr is removed by trituration in ethylacetate and filtration. On concentration in vacuo 1-benzyl-imidazole is obtained as an orange oil.

A mixture of 1-benzyl-imidazole (5 g, 32 mmol), formaldehyde 37% (10 ml, 134 mmol) and sodium hydroxide (100 mg) is refluxed for 7 days and is extracted with ethylacetate. Concentration in vacuo yields 1-benzyl-2-hydroxymethyl-imidazole.

A solution of 1-benzyl-2-hydroxymethyl-imidazole (6 g, 32 mmol) in methylenechloride is slowly added thionylchloride (3.5 ml, 48 mmol) and after stirring at ambient temperature for 4 hours the reaction mixture is concentrated in vacuo yielding 1-benzyl-2-chloromethyl-imidazole, hydrochloride.

A solution of benz[cd]indol-2(1H)-one (4.23 g, 25 mmol) in 50 ml absolute tetrahydrofuran is slowly added to an ice cooled suspension of lithiumaluminumhydride (2 g, mmol) in 50 ml absolute tetrahydrofuran. The mixture is stirred at room temperature over night and is heated to 60° C. and stirred for 5 hours. The reaction is quenched by addition of 2 ml water, 2 ml 15% sodiumhydroxide and 4 ml water, and the heterogenous mixture is filtered and the filtrate is concentrated in vacuo. The remanence is recrystallized from ethanol/water yielding grey hygroscopic crystals.

d: 1-Methyl-2-(N-(4-fluorophenyl)-N-benzyl-methanamine)-4,5-dihydro-imidazole, hydrochloride A mixture of 1-methyl-2-chloromethyl-imidazoline, hydrochloride (0.63 g, 3.7 mmol) and N-benzyl-4-fluoroaniline (1.9 g, 9.3 mmol) in 10 ml absolute ethanol, is heated under a nitrogen atmosphere to 110° C. and the ethanol is distilled of. The mixture is maintained at 110° C. for 3 hours and after cooling to room temperature the crude product is added 25 ml of sodium hydrogencarbonate solution and the excess of N-benzyl-4-fluoroaniline is extracted with diethylether. The water phase is extracted several times using methylenechloride and the combined methylenechloride phases are concentrated in vacuo leaving an oil which on trituration with diethylether yields the title compound as hygroscopic slightly brownish crystals. Mp 185°–186° C.

The following compounds are prepared in a similar way using an appropriate 1-alkyl-2-chloromethyl-imidazoline, hydrochloride and an appropriate amine both as prepared under example 2a and 2b, or by using 1-benzyl-2-chloromethyl-imidazole, hydrochloride as prepared under example 2c.

1-Ethyl-2-(N-phenyl-N-benzyl-methanamine)-4,5-dihydro-imidazole, hydrochloride. Mp 154°–156° C.
1-Propyl-2-(N-phenyl-N-benzyl-methanamine)-4,5-dihydro-imidazole, hydrochloride. Mp 66°–68° C.
1-butyl-2-(N-phenyl-N-benzyl-methanamine)-4,5-dihydro-imidazole, hydrochloride. Mp 62°–63° C.
1-Pentyl-2-(N-phenyl-N-benzyl-methanamine)-4,5-dihydro-imidazole, hydrochloride. Mp 62°–63° C.
1-Hexyl-2-(N-phenyl-N-benzyl-methanamine)-4,5-dihydro-imidazole, hydrochloride. Mp 58°–59° C.
1-Heptyl-2-(N-phenyl-N-benzyl-methanamine)-4,5-dihydro-imidazole, hydrochloride. Mp 75°–76° C.
1-Nonyl-2-(N-phenyl-N-benzyl-methanamine)-4,5-dihydro-imidazole, hydrochloride. Mp 138°–139° C.
1-Butyl-2-(N-(2-pyridyl)-N-benzyl-methanamine)-4,5-dihydro-imidazole, hydrochloride. Mp 63°–65° C.
1-Butyl-2-(N-phenyl-N-(1-phenylethyl)-methanamine)-4,5-dihydro-imidazole, hydrochloride. Mp 165°–167° C.
1-Butyl-2-(N-(4-fluorophenyl)-N-(4'-fluorobenzyl)-methanamine)-4,5-dihydro-imidazole, hydrochloride. Mp 123°–125° C.
1-Butyl-2-(N-(4-fluorophenyl)-N-(1-phenylethyl)-methanamine)-4,5-dihydro-imidazole, hydrochloride. Mp 165°–167° C.
1-Butyl-2-(N-(4-fluorophenyl)-N-benzyl-methanamine)-4,5-dihydro-imidazole, hydrochloride. White crystals. Mp 95°–97° C.
(5H-Dibenz(b,f)azepin-1-yl)-methyl-1-butyl-4,5-dihydro-imidazole, hydrochloride. Mp 106° C.

1-butyl-2-(N-phenyl-N-cyclohexylmethyl-methanamine)-4,5-dihydro-imidazole, hydrochloride. Mp 113°–116° C.

1-butyl-2-(N,N-dibenzyl-methanamine)-4,5-dihydro-imidazole, hydrochloride. Mp 68°–69° C.

1-butyl-1-(N-(4-trifluoromethylphenyl)-N-benzyl-methanamine)-4,5-dihydro-imidazole, hydrochloride. Oil.

1-butyl-2-(N-(4-methoxyphenyl)-N-benzyl-methanamine)-4,5-dihydro-imidazole, hydrochloride. Hygroscopic crystals.

1-butyl-2-(N-(2,4-difulorphenyl)-N-benzyl-methanamine)-4,5-dihydro-imidazole, hydrochloride. Mp 106° C.

1-butyl-2-(N-(2,4-dichlorophenyl)-N-benzyl-methanamine)-4,5-dihydro-imidazole, hydrochloride. Mp 86°–87° C.

1-butyl-2-(N-cyclohexyl-N-benzyl-methanamine)-4,5-dihydro-imidazole, hydrochloride. Mp 120°–125° C.

1-butyl-2-(4-trifluoromethylphenyl)-N-(4-trifluoromethylphenyl-methyl)-methanamine)-4,5-dihydro-imidazole, hydrochloride. Mp 81°–85° C.

1-benzyl-2-(N-propargyl-N-benzyl-methanamine)-4,5-dihydro-imidazole, hydrochloride. Hygroscopic crystals.

1-benzyl-2-(N-phenyl-N-benzyl-methanamine)-4,5-dihydro-imidazole, hydrochloride. Hygroscopic crystals.

1-benzyl-2-(N-(4-fluorophenyl)-N-benzyl-methanamine)-4,5-dihydro-imidazole, hydrochloride. Mp 54° C.

1-benzyl-2-(N-(4-trifluoromethylphenyl)-N-benzyl-methanamine)-4,5-dihydro-imidazole, hydrochloride. Hygroscopic crystals.

N-((2-butyl-3,4-dihydro-imidazolyl)-methyl)-benz[c-d]indol(1H), hydrochloride. Hygroscopic crystals.

1-butyl-2-(N-phenyl-N-(4-nitrophenyl-methyl)-methanamine)-4,5-dihydro-imidazole, hydrochloride. Mp 51°–52° C.

1-butyl-2-(N-phenyl-N-(3-nitrophenyl-methyl)-methanamine)-4,5-dihydro-imidazole, hydrochloride. Mp 58° C.

1-butyl-2-(N-(3-methylcarboxy-phenyl)-N-benzyl-methanamine)-4,5-dihydro-imidazole, hydrochloride. Mp 96°–98° C.

(5H-Dibenz(b,f)azepin-1-yl)-methyl-1-butyl-4,5-dihydro-imidazole, hydrochloride. Dec. 180°–185° C.

1-butyl-2-(N-(3-nitrophenyl)-N-benzyl-methanamine)-4,5-dihydro-imidazole, hydrochloride. Mp 139°–142° C.

1-butyl-2-(N-(2,4,6-trimethyl-phenyl)-N-benzyl-methanamine)-4,5-dihydro-imidazole, hydrochloride. Mp 161°–162° C.

1-Heptyl-2-(N-(2,4-dichlorophenyl)-N-benzyl-methanamine)-4,5-dihydro-imidazole, hydrochloride. Mp 120°–121° C.

1-Butyl-2-(1-methyl-N-phenyl-N-benzyl-methanamine)-4,5-dihydro-imidazole, hydrochloride. Hygroscopic crystals.

1-butyl-2-(N-(4-nitrophenyl)-N-benzyl-methanamine)-4,5-dihydro-imidazole, hydrochloride. Mp 48°–51° C.

1-butyl-2-(N-phenyl-N-(3-methoxyphenyl-methyl)-methanamine)-4,5-dihydro-imidazole, hydrochloride. Mp 138° C.

1-Butyl-2-(N-(2,4-dichlorophenyl)-N-cyclohexylmethyl-methanamine)-4,5-dihydro-imidazole, hydrochloride. Hygroscopic crystals.

1-Butyl-2-(N-(2,4-dibromophenyl)-N-benzyl-methanamine)-4,5-dihydro-imidazole, hydrochloride. Mp 130°–135° C.

1-Butyl-2-(N-phenyl-N-(2-furanyl)-methanamine)-4,5-dihydro-imidazole, hydrochloride. Mp 104°–108° C.

1-Butyl-2-(N-phenyl-N-(2-phenyl-ethyl)-methanamine)-4,5-dihydro-imidazole, hydrochloride. Mp 153° C.

2-(N-phenyl-N-benzyl-methanamine)-benzimidazole, hydrochloride. Decomposes at 100° C.

1-Butyl-2-(N-(3-methoxyphenyl)-N-benzyl-methanamine)-4,5-dihydro-imidazole, hydrochloride. Hygroscopic crystals.

1-Butyl-2-(N-phenyl-N-(4-methoxyphenyl-methyl)-methanamine)-4,5-dihydro-imidazole, hydrochloride. Hygroscopic crystals.

1-Butyl-2-(N-phenyl-N-(3-pyridyl-methyl)-methanamine)-4,5-dihydro-imidazole, hydrochloride. Mp 66°–68° C.

1-Benzyl-2-(N-phenyl-N-benzyl-methanamine)-imidazole, oxalate

After cooling to ambient temperature the crude product is taken up in ethanol and the mixture is made alkaline by adding 30% sodium hydroxide solution. After concentration in vacuo the mixture is subjected to column chromatography using ethylacetate added 0.1% triethylamine as eluent. The fractions containing the product are concentrated in vacuo and the product is triturated with a saturated solution of oxalic acid in water. The formed white crystals are isolated, Mp 68°–70° C.

1-Butyl-2-(N-phenyl-N-benzyl-methanamine)-benzimidazole, hydrochloride

A solution of 2-(N-phenyl-N-benzyl-methanamine)-benzimidazole (prepared by reacting N-benzyl-aniline and 2-chloromethyl-benzimidazole, hydrochloride in the same way as described in example 2d) (1.2 g, 3.8 mmol) and n-butylbromide (0.54 ml, 5 mmol) in 10 ml absolute dimethylforamide is added sodiumhydride (5 mmol). The mixture is stirred over night, quenched by addition of ice and the product is extracted with diethyl ether. The ether phase is washed with water, dried and evaporated in vacuo. The resulting oil is triturated with 15 ml 4M HCl and the formed crystals is filtered off and recrystallized from acetonitrile yielding slightly green crystals. Mp 128°–130° C.

We claim:

1. A compound having the formula

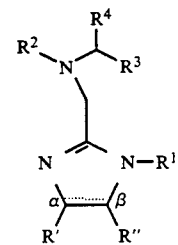

wherein

R$^1$ is C$_{2-10}$ saturated or unsaturated alkyl or

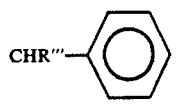

wherein R''' is H or

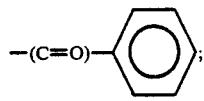

$R^2$ is phenyl which is unsubstituted or substituted one or more times with halogen, $CF_3$, $C_{1-6}$-alkoxy, $NO_2$, $CO_2$—$C_{1-6}$-alkyl, methyl; benzyl which is unsubstituted or substituted one or more times with halogen, $CF_3$, $C_{1-6}$-alkoxy, $NO_2$, $CO_2$—$C_{1-6}$-alkyl, methyl; or cyclohexyl;

$R^3$ is phenyl which is unsubstituted or substituted one or more times with halogen, $CF_3$, $C_{1-6}$-alkoxy, $NO_2$, $CO_2$—$C_{1-6}$-alkyl, methyl; naphthyl which is unsubstituted or substituted one or more times with halogen, $CF_3$, $C_{1-6}$-alkoxy, $NO_2$, $CO_2$—$C_{1-6}$-alkyl, methyl; $C_{1-6}$ unsaturated alkyl;

$R^4$ is H, $C_{1-6}$-alkyl, or benzyl;

R' and R'' are each hydrogen

2. A compound of claim 1 which is 1-benzyl-2-(N-phenyl-N-(phenylmethyl)-methanamine)-4,5-dihydro-imidazole.

3. A compound of claim 1 which is 1-propargyl-2-(N-phenyl-N-(phenylmethyl)-methanamine)-4,5-dihydro-imidazole.

4. A compound of claim 1 which is 1-(α-benzoylbenzyl)-2-(N-phenyl-N-(phenylmethyl)-methanamine)-4,5-dihydro-imidazole.

5. A compound of claim 1 which is 1-butyl-2-(N-phenyl-N-(phenylmethyl)-methanamine)-4,5-dihydro-imidazole.

6. The method of treating an indication relating to or arising from Ca overload in brain cells comprising the step of administering to a person in need of treatment an effective Ca overload-blocking amount of a compound having the formula

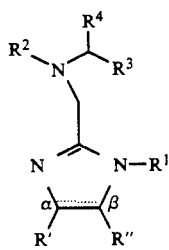

wherein
$R^1$ is $C_{1-10}$-alkyl which is unbranched or branched; $C_{2-10}$-alkenyl or

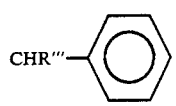

wherein R''' is H or

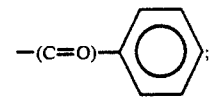

$R^2$ is phenyl which is unsubstituted or substituted one or more times with halogen, $CF_3$, $C_{1-6}$-alkoxy, $NO_2$, $CO_2$—$C_{1-6}$-alkyl, methyl; benzyl which is unsubstituted or substituted one or more times with halogen, $CF_3$, $C_{1-6}$-alkoxy, $NO_2$, $CO_2$-$C_{1-6}$-alkyl, methyl; or cyclohexyl;

$R^3$ phenyl which is unsubstituted or substituted one or more times with halogen, $CF_3$, $C_{1-6}$-alkoxy, $NO_2$, $CO_2$—$C_{1-6}$-alkyl, methyl; naphthyl which is unsubstituted or substituted one or more times with halogen, $CF_3$, $C_{1-6}$-alkoxy, $NO_2$, $CO_2$—$C_{1-6}$-alkyl, methyl; $C_{1-6}$ unsaturated alkyl;

$R^4$ is H, $C_{1-6}$-alkyl, or benzyl;

R' and R'' are each hydrogen or a pharmaceutically-acceptable addition salt thereof.

7. A pharmaceutical preparation for the treatment of an indication relating to or arising from Ca overload in brain cells comprising an effective Ca overload-blocking amount of a compound of the formula

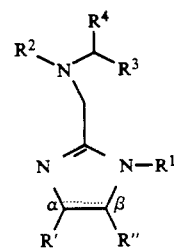

wherein
$R^1$ is $C_{1-10}$-alkyl which is unsubstituted or branched; $C_{2-10}$-alkenyl or

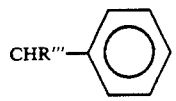

wherein R''' is H or

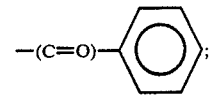

$R^2$ is phenyl which is unsubstituted or substituted one or more times with halogen, $CF_3$, $C_{1-6}$-alkoxy, $NO_2$, $CO_2$—$C_{1-6}$-alkyl, methyl; benzyl which is unsubstituted or substituted one or more times with halogen, $CF_3$, $C_{1-6}$-alkoxy, $NO_2$, $CO_2$-$C_{1-6}$-alkyl, methyl; or cyclohexyl;

$R^3$ phenyl which is unsubstituted or substituted one or more times with halogen, $CF_3$, $C_{1-6}$-alkoxy, $NO_2$, $CO_2$—$C_{1-6}$-alkyl, methyl; naphthyl which is unsubstituted or substituted one or more times with halogen, $CF_3$, $C_{1-6}$-alkoxy, $NO_2$, $CO_2$—$C_{1-6}$-alkyl, methyl; $C_{1-6}$ unsaturated alkyl;

$R^4$ is H, $C_{1-6}$-alkyl, or benzyl;

R' and R'' are each hydrogen or a pharmaceutically-acceptable addition salt thereof, and a pharmaceutically-acceptable carrier or diluent therefor.

8. A method of claim 6 wherein the compound is 1-benzyl-2-(N-phenyl-N-(phenylmethyl-methanamine)-4,5-dihydro-imidazole.

9. A method of claim 6 wherein the compound is 1-propargyl-2-(N-phenyl-N-(phenylmethyl)-methanamine)-4,5-dihydro-imidazole.

10. A method of claim 6 wherein the compound is 1-(α-benzoyl-benzyl)-2-(N-phenyl-N-(phenylmethyl)-methanamine)-4,5-dihydroimidazole.

11. A method of claim 6 wherein the compound is 1-butyl-2-(N-phenyl-N-(phenylmethyl)-methanamine)-4,5-dihydro-imidazole.

12. A preparation of claim 7 wherein the compound is 1-benzyl-2-(N-phenyl-N-(phenylmethyl)-methanamine)-4,5-dihydro-imidazole.

13. A preparation of claim 7 wherein the compound is 1-propargyl-2(N-phenyl-N-(phenylmethyl)-methanamine)-4,5-dihydro-imidazole.

14. A preparation of claim 7 wherein the compound is 1-(α-benzoylbenzyl)-2-(N-phenyl-N-(phenylmethyl)-methanamine)-4,5-dihydro-imidazole.

15. A preparation of claim 7 wherein the compound is 1-butyl-2-(N-phenyl-N-(phenylmethyl)-methanamine)-4,5-dihydro-imidazole.

16. The method of claim 6, wherein the indication treated is selected from anoxia, ischemia, migraine, and neurode-generative changes connected with the same.

17. The pharmaceutical composition of claim 7, wherein the indication for which said pharmaceutical composition is useful is selected from anoxia, ischemia, migraine, and neurode-generative changes connected with the same.

* * * * *

UNITED STATES PATENT AND TRADEMARK OFFICE
CERTIFICATE OF CORRECTION

PATENT NO. : 5,296,493

DATED : March 22, 1994

INVENTOR(S) : Peter Moldt and Elsebet Ø. Nielsen

It is certified that error appears in the above-indentified patent and that said Letters Patent is hereby corrected as shown below:

Title page, [57], Col. 2, line 3; "$C_{1-10}$ saturated" should read -- $C_{2-10}$ saturated --.
Title page, [57], Col. 2, line 7; change "is unsubstituted or" to -- may be --.
Title page, [57], Col. 2, line 13; change "is unsubstituted or" to -- may be --.
Col. 1, line 44; insert a semicolon after "alkyl".
Col. 3, lines 46 and 47; "Ci/g; (calcium chloride)" should read -- Ci/g (calcium chloride); --.
Col. 5, line 2; "hours" should read -- hour --.
Col. 5, line 31; "A solution" should read -- To a solution --.
Col. 5, line 33; delete the hyphen between "hydrogen" and "chloride".
Col. 5, line 35; "20° C." should read -- -20° C. --.
Col. 5, line 46; insert -- an -- before "additional" and change "hour" to -- hours --.
Col. 5, line 48; "of" should read -- off --.
Col. 5, line 53; "hexyle-" should read -- hexyl- ".
Col. 5, line 54; "thylenediamine" should read -- ethylenediamine --, and "nonyle-" should read -- nonyl- --.
Col. 5, line 55; "thylenediamine" should read -- ethylenediamine --.
Col. 6, line 15; "the to phases" should read -- the two phases --.
Col. 6, line 17; "phases is washed" should read -- phases are washed --.
Col. 6, line 25; "filtered of" should read -- filtered off --.
Col. 6, lines 33 and 34; "Finally is the mixture stirred" should read -- Finally the mixture is stirred --.
Col. 6, line 35; "remanecens" should read -- residue --.
Col. 7, line 40; "phases is washed" should read -- phases are washed --.

UNITED STATES PATENT AND TRADEMARK OFFICE
CERTIFICATE OF CORRECTION

PATENT NO. : 5,296,493
DATED : March 22, 1994
INVENTOR(S) : Peter Moldt and Elsebet Ø. Nielsen It is certified that error appears in the above-indentified patent and that said Letters Patent is hereby corrected as shown below:

Col. 8, line 13; "remanence" should read -- residue --.
Col. 8, line 23; "distilled of." should read -- distilled off. --.
Col. 8, line 25; insert -- to -- after "added".
Col. 9, line 6; "1-butyl-1-(N" should read -- 1-butyl-2-(N --.
Col. 9, line 12; "difulorphenyl" should read -- difluorophenyl --.
Col. 9, line 20; "1-butyl-2-(4" should read -- 1-butyl-2-(N-(4 --.
Col. 10, line 49; "crystals is filtered" should read -- crystals are filtered --.
Col. 10, lines 55 to 65; in the formula, remove the dotted line between "α" and "ß".
Col. 10, line 68; insert a semicolon after "alkyl".
Col. 11, lines 28 and 29; insert a line between these two lines which reads -- or a pharmaceutically-acceptable addition salt thereof. --.

UNITED STATES PATENT AND TRADEMARK OFFICE
CERTIFICATE OF CORRECTION

PATENT NO. : 5,296,493
DATED : March 22, 1994
INVENTOR(S) : Peter Moldt and Elsebet Ø. Nielsen It is certified that error appears in the above-indentified patent and that said Letters Patent is hereby corrected as shown below:

Col. 11, lines 47 to 57; in the formula, remove the dotted line between "α" and "ß".
Col. 11, lines 60 and 61; these lines should read -- $R^1$ is $C_{2-10}$ saturated or unsaturated alkyl; or --.
Col. 12, lines 27 to 37; in the formula, remove the dotted line between "α" and "ß".
Col. 12, lines 39 and 40; these lines should read -- $R^1$ is $C_{2-10}$ saturated or unsaturated alkyl; or --.
Col. 13, line 12; insert a hyphen between "dihydro" and "imidazole".
Col. 14, line 11; insert -- and -- before "migraine".
Col. 14, line 15; insert -- and -- at the end of the line after "ischemia,".

Signed and Sealed this

Eighteenth Day of October, 1994

Attest:

BRUCE LEHMAN

Attesting Officer    Commissioner of Patents and Trademarks